United States Patent [19]

Holfelder et al.

[11] Patent Number: 4,502,939
[45] Date of Patent: Mar. 5, 1985

[54] ELECTROCHEMICAL OXYGEN SENSOR, PARTICULARLY FOR ANALYSIS OF COMBUSTION CASES FROM INTERNAL COMBUSTION ENGINES

[75] Inventors: Gerhard Holfelder, Ditzingen; Klaus Müller, Tamm, both of Fed. Rep. of Germany

[73] Assignee: Robert Bosch GmbH, Stuttgart, Fed. Rep. of Germany

[21] Appl. No.: 572,595

[22] Filed: Jan. 19, 1984

Related U.S. Application Data

[63] Continuation of Ser. No. 260,258, May 4, 1981, abandoned.

[30] Foreign Application Priority Data

May 10, 1980 [DE] Fed. Rep. of Germany ....... 3017947

[51] Int. Cl.³ ............................................. G01N 27/46
[52] U.S. Cl. .................................. 204/429; 204/1 T; 204/425; 204/426; 204/427; 204/428; 156/89; 264/61; 427/126.5
[58] Field of Search ................ 204/1 S, 421, 424–429

[56] References Cited

U.S. PATENT DOCUMENTS

| | | | |
|---|---|---|---|
| 4,101,403 | 7/1978 | Kita et al. | 204/410 |
| 4,157,282 | 6/1979 | Riddel | 204/426 |
| 4,282,080 | 8/1981 | Müller et al. | 204/428 |
| 4,294,679 | 10/1981 | Maurer et al. | 29/592 R |
| 4,300,990 | 11/1981 | Maurer | 204/425 |
| 4,310,401 | 1/1982 | Stahl | 204/428 |
| 4,334,974 | 6/1982 | Müller et al. | 204/425 |
| 4,356,065 | 10/1982 | Dietz | 204/1 S |

FOREIGN PATENT DOCUMENTS 1380936 4/1973 U.S.S.R. .......................... 204/195 S

*Primary Examiner*—T. Tung
*Attorney, Agent, or Firm*—Frishauf, Holtz, Goodman & Woodward

[57] ABSTRACT

To provide access of gases to an electrode (39, 48) positioned on a flat plate (35) of solid electrolyte material, under controlled conditions, and while preventing access of gases to the electrodes where not desired, the electrodes are covered with a porous cover layer (42, 49) of sintered granular material, for example of zirconium dioxide, having a grain size of 10 μm, and 25 μm thick, with void or pore-formation material added thereto which, upon sintering, becomes volatile and leaves a porous structure. A gas-tight tunnel covering (44, 51) extends over the electrode and filler covering leaving an open space in those regions where the electrode is exposed to the desired gas, for example a test gas adjacent the sensing end (11/1) of the sensor, or oxygen from ambient air adjacent the connecting or terminal end (11/3) of the sensor, the respective gas to be applied to the electrode diffusing through the pores of the porous structure to the respective electrode.

12 Claims, 5 Drawing Figures

ELECTROCHEMICAL OXYGEN SENSOR, PARTICULARLY FOR ANALYSIS OF COMBUSTION CASES FROM INTERNAL COMBUSTION ENGINES

This application is a continuation of application Ser. No. 260,258, filed May 4, 1981, now abandoned.

Cross Reference to Related patents and Applications

U.S. Pat. No. 4,157,282, RIDDEL.

DE-OS No. 27 11 880, to which U.S. Ser. No. 213,049, filed Dec. 4, 1980, DIETZ, now U.S. Pat. No. 4,356,065, corresponds.

DE-OS 29 09 452, to which U.S. Ser. No. 121,632, filed Feb. 14, 1980 Müller et al, now U.S. Pat. No. 4,282,080, corresponds DE-OS No. 29 13 866, to which U.S. Ser. No. 121,599, filed Feb. 14, 1980. MAURER, now U.S. Pat. No. 4,300,990 corresponds, DE-OS 29 28 496, to which U.S. Ser. No. 145,738, filed May 1, 1980, MAURER et al, now U.S. Pat. No. 4,294,679 corresponds DE-OS 29 37 048, to which U.S. Ser. No. 181,841, filed Aug. 27, 1980, STAHL, now U.S. Pat. No. 4,310,401 corresponds.

The present invention relates to electrochemical sensors to sense and analyze the composition of gases with respect to their oxygen content, and more particularly to such sensors to determine the oxygen content in exhaust gases resulting from combustion processes, and especially from internal combustion engines, and method of their manufacture.

Background

Basically, two types of sensors using a solid ion conductive electrolyte are used, one operating on the potentiometric principle, in which the sensor functions like a fuel cell providing a voltage output when exposed, respectively, to a reducing gas and a reference gas containing oxygen, for example ambient air, and no, or only very low, output, when the test gas contains oxygen. The voltage jump at the transition provides an indication of the transition of the gas to be analyzed between reducing and oxidizing state. The other type of sensor operates in the polarographic mode: a voltage is applied across the electrodes and, depending on the conversion of oxygen molecules at the cathode electrode, a current will flow which, if all the oxygen molecules reaching the cathode electrode can be converted, will be representative of the oxygen concentration in the gas to be analyzed. This current is the limiting current, and the sensor requires application of a d-c bias voltage, for example in the order of between 0.1 to 1 V. These sensors can be installed in the exhaust system from internal combustion engines retained in suitable housing structures. Sensors in which both electrodes are exposed to the exhaust gases, for example sensors operating in the polarographic mode, have a lower voltage output than sensors in which one of the electrodes has a reference gas, for example the oxygen in ambient air, applied thereto. Separation of the sensor electrodes from each other such that only one is exposed to the gas to be analyzed, whereas the other is exposed to ambient air, introduces difficulties in construction. One construction uses a closed tube; for manufacturing and cost reasons, however, as well as for reliability in operation, plate-like sensing elements are preferred.

The Invention

It is an object to provide an oxygen sensor which is capable of using plate-like electrodes which can easily be made under mass production conditions and which provides for separation of gases applied to respective electrodes, that is, for example oxygen from ambient air to one electrode, and the gas to be analyzed, typically the exhaust gas from an internal combustion engine, to the other.

Briefly, a plate-like solid ion conductive body, for example of stabilized zirconium dioxide, is used as the sensing element, which has flat electrodes applied to one or respective major surfaces of the plate, set back from the edges of the plate. Gas is conducted to the respective electrodes through a porous sintered body of filler material applied over the respective electrode. The electrodes are covered with a gas-tight covering placed over the filler material covering the electrode, and mechanically supported thereby, the gas-tight covering leaving exposed a portion of the filler material to permit exposure of the porous sintered filler material to the gas which is to be conducted to the electrodes therethrough. Thus, for example, the sensing electrode is left free from the gas-tight covering at the tip or sensing end exposed to the exhaust gases, whereas the other, or reference electrode can receive oxygen from ambient air through an exposed strip near the connecting end of the sensor construction, the oxygen being conducted to the respective electrode through the porous sintered filler material, and shielded from contamination by the exhaust gases in the region thereof by the gas-tight covering which is applied over that region of the gas-pervious filler material. The gas-pervious filler material thus extends into an open tunnellike construction over the electrodes, the tunnel providing access to the gas and being filled by the sintered porous gas-pervious filler material.

The sensor plate can easily be secured within a metal housing, particularly adapted for use with automotive engines. The sensor construction has the advantage that the output signal can have a substantial strength since one of the electrodes is exposed to a reference gas and the other to the gas to be analyzed, while still permitting ready industrial mass production of the sensor. The hollow tunnel space beneath the gas-tight covering will be essentially flat and can be subdivided by support strips or ridges, in transverse section, to insure stability to the entire structure. The sensor element thus will be highly stable, and particularly with respect to changing temperatures and temperature gradients; further, the structure is resistant to deterioration or breakage due to vibration and shock, and is thus particularly suitable for the rough and severe operating environments in automotive vehicles. The hollow tunnel spaces are filled with porous material which, by suitable choice, can act as a diffusion barrier for oxygen molecules to control the migration of oxygen molecules therethrough, so that sensors operating in accordance with polarographic principle can be constructed thereby, providing limiting currents which are, essentially, analog representations of the oxygen content of the sensing gas. The spaces beneath the tunnels, and filled with the sintered porous filler materials, can also serve as supply ducts or channels for the reference gas. For sensors operating in the potentiometric mode, the spaces can be used to supply the gas to be analyzed to the sensing electrode while additionally protecting the electrode with respect to the hot and chemically aggressive exhaust gases, and can also serve as supply ducts or channels for the reference gas.

In accordance with a feature of the invention, the sensor is made by applying, sequentially, the electrodes, material which will form a porous cover layer by including a volatile pore-forming substance therein, and thereover the material to form the gas-tight cover, and then sintering the entire composit at an elevated temperature to sinter together the respective layers and form the gas-tight covering as well as the porous layer in the sintering step.

Drawings

Figure 1:
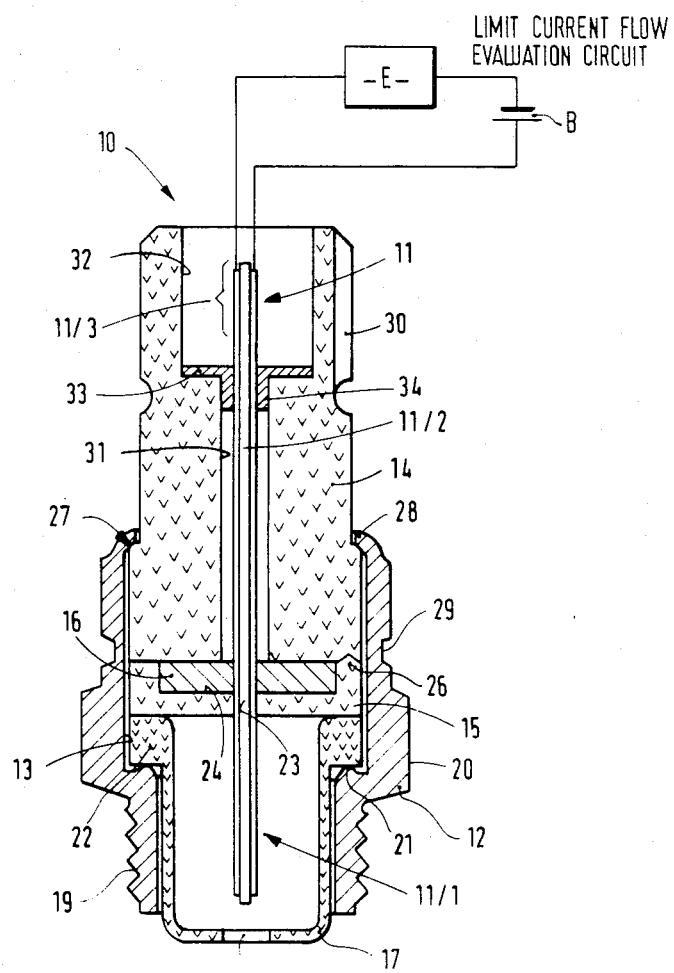
FIG. 1 is a highly schematic longitudinal view through a sensor operating in the polarographic mode and utilizing oxygen of ambient air as a reference material, omitting elements not necessary for an understanding of the invention.

The sensor 10 (FIG. 1) is particularly suitable to determine the oxygen content in the exhaust gases from automotive-type internal combustion engines. A battery B provides a bias voltage; it is connected to the electrodes through a limit current flow evaluation circuit E which, in its simplest form, is a milliammeter which provides an output indication of the limit current flow under varying oxygen content from the exhaust gases of the engine.

The sensor 10, in general, has a plate-like sensing element 11, and is secured in a housing 12, preferably made of metal. The housing 12 includes two securely retained ceramic holding elements 14, 15 and a seal 16. A protective shield 17 with an opening 18 therein to receive exhaust gases surrounds the sensor at the sensing end portion 11/1 thereof.

The metal housing 12 has an external thread 19 with which it can be screwed into a suitably tapped opening in the exhaust pipe or exhaust manifold leading combustion gases from an internal combustion engine. The housing is formed with an engagement portion 20 for a wrench. The housing has a longitudinal bore or opening 13 which is formed with a shoulder 21 on which a flange 22 of the protective shroud or sleeve 17 is seated. The shroud or sleeve 17 is made of ceramic; it may, however, be made of different heat-resistant materials, for example corrosion-resistant steel, suitably secured to the metal housing shell 12. More than one gas inlet opening 18 may be formed, and the openings can be additionally shaped to direct exhaust gases to the sensor 11. The lower side of the flange 22 is seated on the shoulder 21 of the housing. The upper side of the flange 22 is engaged by the ceramic holder 15. Ceramic holder 15 has a central opening 23 and a pocket 24 formed therein to receive a seal 16 to seal the sensor 11 in position. Suitable seals are cements, glass, glass ceramic, or similar materials. The plate-like sensor has lateral notches 25 (FIGS. 2, 3) formed therein to insure longitudinal placement of the sensor in position in the housing, and anchor the sensor in place. The seal 16 subdivides the sensor into—with respect to FIG. 1—a lower or sensing portion 11/1 and an intermediate or holder portion 11/2. The holder 14, also of ceramic, is engaged at its lower side on the holder ceramic disk 15 and on the seal 16. Rotation of the two ceramic elements 15, 16 is prevented by forming a projection 26 in the disk 16, engaging a matching notch in the ceramic element 14. The outside of element 14 is formed with a shoulder 27 over which an in-turned edge of the metal housing 12 extends, to hold the sensor portions together. If necessary, a sealing ring can be interposed between the shoulder 27 and the in-turned edge 28. The sensor can be readily assembled together in accordance with a known hot-shrinking process for tight connection of the elements. In accordance with this process, a groove 29 is formed in the outer surface of the metal housing 12. After assembly of the elements together, that is, in the position shown in FIG. 1, the groove region is heated, for example by an induction coil, and the housing 12 is then longitudinally compressed and permitted to cool while maintaining the compression force.

An attachment groove 30 is formed in the upper end of the ceramic element 14 to insure correct positioning of an electrical terminal—not shown. A central opening 31 is formed in the ceramic element 14, in alignment with the opening 23 of the holder 15. The portion 11/2 of the sensor element 11 passes through the opening 31. The opening 31 is enlarged at its terminal end as seen at 32, and the sensor terminal or connecting portion 11/3 extends into the opening 32. A guide bushing 33 locates the sensor 11 in position in the opening 31. The guide bushing 33, preferably, is a thermosetting resin bushing having a guide extension portion 34 which fits into the opening 31 and seals off the opening 32 while, simultaneously, locating the terminal or connecting portion 11/3 of the sensor element 11.

The particular construction of the sensor element within the housing does not form part of the present invention; the arrangement illustrates a preferred form; various other arrangements and ways of securing the sensor element 11 in position within a housing may be used.

The longitudinal plate-like sensor element 11 has an oxygen ion conductive solid electrolyte, for example a stabilized zirconium dioxide plate-like carrier 35. A suitable carrier is about 5 cm long, 8 mm wide, and 1 mm thick. It has two major surfaces 36 FIG. 2, and 45—FIG. 3. Surface 36 is covered with an electrically insulating layer 37 leaving, however, a window 38 where the underlying zirconium dioxide of the surface 36 of the solid electrolyte plate 35 is exposed. The electrically insulating layer 37 is made of aluminum oxide and about 15 $\mu$m thick. The window 38 is positioned in the sensing portion 11/1. The window 38 is 4 mm wide and 12 mm long. A sensing or measuring electrode 39 is applied in the region of the window 38 on the surface 36 of the carrier 35. The sensing electrode is made of porous platinum and has a thickness of 8 $\mu$m. A conductive track 39' extends to the connecting portion 11/3, over the insulating layer 37. The measuring electrode 39 as well as the associated track 39' which, preferably, also is made of platinum, can be applied to the sensor element by any suitable and known process, most suitably by a screen-printing. The electrode 39 is located behind the terminal edge 40 of carrier 35. A layer-like heating element 41 made of a platinum track is applied to the region laterally of the window 38 over the insulating layer 37, and reaching around the end 40 of the sensing end or edge portion as well. The heating element track 41 is preferably a platinum layer of 12 μm thickness and arranged in undulating or meander form. It is connected by conductive tracks 41/1 and 41/2, also extending over the insulating layer 37 at both sides of the sensing electrode conductive track 39'. The connecting tracks 41/1 and 41/2 likewise are of platinum, and provide for electrical connection of the platinum heater track 41 to the connecting or terminal region 11/3 of the sensor 11.

In accordance with the invention, a coarsely porous sintered filler material 42 is applied over the sensing electrode 39 or over the entire window 38, respectively, filling the space left free by the electrically insulating layer 37 and covers the zone between the window 38 and the end 40 of the sensing end portion. This coarse porous insulating filler 42 may consist of zirconium dioxide with a grain size of 10 μm, and has a thickness of 25 μm. The porous filler 42, during manufacture, includes additionally a pore-forming substance—not shown—which consists of a material which becomes volatile and escapes during sintering; a suitable material, for example, is polyurethane granulate. The filler 42, together with the void-forming additive, is applied over the respective region by any well known process, suitably by screen-printing. In accordance with a further feature of the invention, a gas-tight tunnel covering 44 is applied over the sensing end portion 11/1 leaving, however, a strip 43 of about 1 mm width free, extending parallel to the end 40 of the sensing end portion 11/1. The edge of the tunnel covering 44 is forward of the edge of electrode 39, to force the gas to flow at least some distance along the plane of the carrier 35 (see FIG. 2). The gas-tight covering 44 is made of aluminum oxide or magnesium spinel and has thickness of 40 μm. The gas-tight covering 44 also covers the heating element 41 and protects the heating element track from the hot gases to be analyzed. The filler 42 within the tunnel formed by the tunnel cover 44 forms an oxygen molecule diffusion barrier controlling diffusion of oxygen molecules to the surface of the electrode. The required diffusion resistance to provide for essentially analog output of current limit flow with respect to oxygen content in the gases can be controlled by suitable selection of the size of the pores of the filler 42, as well as by the length, width, and height of the duct beneath the tunnel covering 44.

Figure 4:
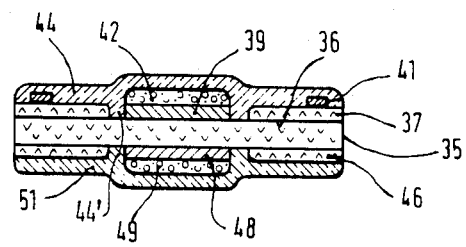
FIG. 4 is a transverse sectional view along the line IV—IV of FIG. 3, to a still more enlarged scale.

The tunnel covering 44 is mechanically supported by the filler material 42 above the electrodes and, as can best be seen in FIG. 4, is supported at the end portions by the insulating material 37 and, where the tunnel is formed, has longitudinal ridges or strips 44' directly engaging the carrier 35 formed by the zirconium dioxide plate.

Figure 2:
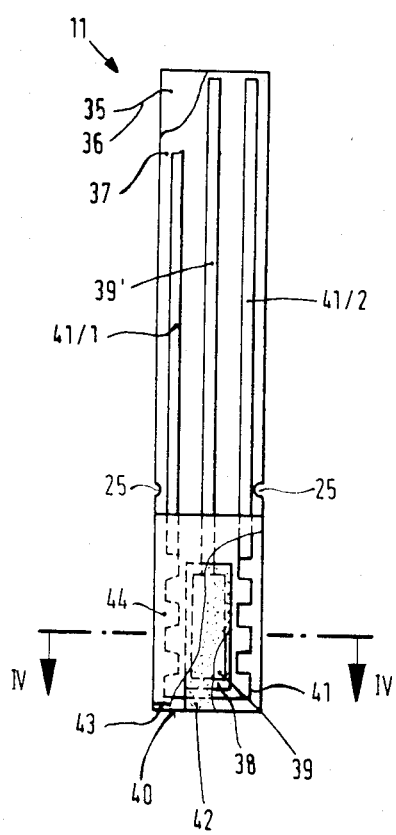
FIG. 2 is a plan view of the sensor element, to an enlarged scale.
Figure 3:
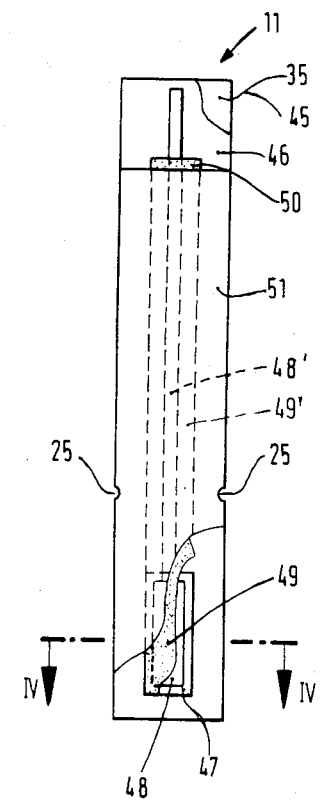
FIG. 3 is a plan view of the reverse side of the sensor element, rotated 180° with respect to FIG. 2.

The second major surface 45 of the carrier 35 is illustrated in FIG. 3. An electrically insulating layer 46 covers the surface 45. Layer 46 corresponds to layer 37 on the first surface 36 (FIG. 2) and, likewise, is made of aluminum oxide, 15 μm thick, applied suitably by screen-printing. The layer 46 has a window 47 which, in size and arrangement, corresponds to the window 38 on the surface 36. A reference electrode 48 is located in the window 47 which corresponds, essentially, both in material and dimensions, to the sensing or measuring electrodes 39 on the first surface 36—FIG. 2, that is, is made of porous platinum having a thickness of 8 μm. A conductive track 48', corresponding to track 39', extends from the electrode 48 to the connecting or terminal end portion 11/3 of the sensor. The track 48' is positioned over the insulating layer 46. The reference electrode 48 may fill the entire window 47 or be slightly smaller. A filler 49 made of highly porous material is located over the electrode 48. Similar to the filler 42, it consists of coarse-grain zirconium dioxide, with a grain size of about 10 μm; the filler may, however, also be applied in the form of one or more superimposed layers or strips. This filler, likewise, when applied will include volatile materials which will form pores or voids. The entire surface is then covered with a gas-tight tunnel covering layer 51, extending over the edge regions, over the insulating layer 46 and over the filler 48 leaving, however, a free strip 50 of filler material 48 adjacent the terminal or connecting end portion 11/3, and sealingly separated from the sensing end portion 11/1 by the seal 16 (FIG. 1). The porous material 49 extends over the window 47 and all the way to the end portion 50, as seen by the broken lines in FIG. 3. The window 47, thus, may be much longer than the window 38, extending up to the connecting or terminal end portions. The tunnel covering 51, like the tunnel covering 44, is made of aluminum oxide, or magnesium spinel, having a thickness of 40 μm.

In accordance with a preferred method of manufacture, all layers on the two major surfaces 36, 45 of the carrier 35 are applied by a well known printing method, screen-printing being particularly suitable. The various layers are applied one after the other, dried at about 100° C. The thus prepared sensing element 11 is then sintered at 1500° C.

The carrier 35 may be presintered at a substantially lower temperature, for example at about between 850°-1000° C., that is, be rendered sufficiently stable and stiff to permit application of the respective layers thereon; this is done in the first sintering step. After application of the respective layers, the zirconium dioxide is then again sintered at the higher temperature, whereupon all the layers are sintered together and the final sintering temperature of the carrier 35 has also been attained.

The sensing gas passage thus permits gas, entering through the opening 18, to pass through the sensing edge region 43 (FIG. 2) and through the porous cover 42 beneath the tunnel covering 44 to reach the electrode 39. Reference gas, for example oxygen of ambient air, will reach the electrode 48 by entering at the open strip 50 into the porous cover 49 to then contact the electrode 48.

The gas-tight layers 44, 49, open to the respective gases at opposite ends, prevent access of the gas to which the respective electrode is not to be exposed to that electrode; thus, the cover 44, open at the end 43, is closed at the terminal or connecting end portion 11/3, but permits access of gas to be analyzed at the sensing end portion 11/1. The gas-tight cover 51 is open at the terminal or connecting end portion 11/3 leaving the strip 50 exposed, but closed at the sensing end portion 11/1.

During sintering, the filler material 42 on the measuring electrode 39 and the filler material 49 on the reference electrode 48 will have become sufficiently porous. By suitable selection of the path length, thickness, and void or pore-causing additives, before sintering, the filler 42 may form a diffusion barrier for oxygen molecules, controlling the diffusion of oxygen molecules from the gas to be analyzed to the sensing electrode 39.

Likewise, the porous filler material 49 will insure that oxygen from ambient air, to which the connecting terminal end portion 11/3 is exposed, can reach the reference electrode 48.

The sensor as described is suitable to measure oxygen content in a gas to be analyzed in accordance with a polarographic principle of measurement. A direct current voltage from battery B is applied across the measuring electrode 39 and the reference electrode 38. The amplitude of the current flowing in the measuring circuit will be a measure of the oxygen content in the gas, which amplitude is evaluated in the limit current flow evaluation circuit E.

For some installations it may be suitable to expose the reference electrode 48 not to oxygen from ambient air. For such use, the filler 49 and the tunnel cover 51 may be omitted. Instead, the reference electrode 48 may also be exposed to the measuring gas. Preferably, it is then made of a porous material such as gold or silver, and covered with a porous protective layer, for example made of aluminum oxide.

Figure 5:
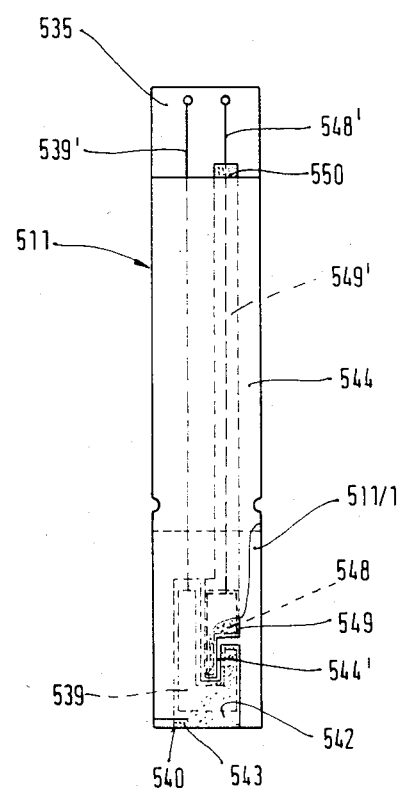
FIG. 5 is a plan view of a sensor showing another embodiment.

It is also possible to so construct the sensor that both the sensing electrode as well as the reference electrode are positioned on the same side of a plate-like carrier. FIG. 5 highly schematically illustrates this embodiment, in which parts similar to those previously described have been given the same reference numerals as before, incremented by 500, and the illustration, for simplicity, has been rendered highly schematic.

Sensing and measuring electrodes 539, 548 are constructed in interdigited form to extend the mutual surface area. The respective electrodes 539, 548 are connected by connecting tracks 539', 548' illustrated, for simplicity, merely as single straight lines to the connecting end of the sensing electrode. The carrier 535 need no longer be made entirely of zirconium dioxide, but rather of a much less expensive insulating plate which, in the region of the electrodes, has a thin solid electrolyte layer 511/1 applied thereto, on which the respective electrodes 539, 548 are applied. A porous layer 542 covers the electrode 539; a similar porous layer 549 covers the electrode 548. The layer are separated by ridges 544' extending between the electrodes. The cover layer 549 has an extension 549' extending towards the terminal or connecting end portion of the sensor, and is exposed at 550 to the oxygen of ambient air. This construction of the sensor uses less of the expensive zirconium dioxide material and permits constructing the carrier 535 of any suitable material, metal or insulating; if metal, an insulating layer similar to layer 37 is applied thereover. After application of the electrodes and of the respective layers 542, 549, 549' thereover, the gas-tight tunnel covering 544 is applied, covering the sensor except for the strip 550 for admission of ambient oxygen from air to the connecting layer 549' and the layer 549 covering the electrode 548, and a strip 543 at the end face 540 of the sensor to permit access of gas to be analyzed to the porous cover 542, and the unit is then sintered, as before.

The heater element 41 (FIG. 2) can be applied to the surface 36, as shown; if needed, a second heater element can be applied to the second surface 45 (FIG. 3); in the embodiment of FIG. 5, the heater element is preferably applied to the back side surface or beneath an insulating layer. For some applications, a heater element may not be needed.

The sensor construction has been described in connection with a polarographic sensor. Similar tunnel-gas conduction arrangements can be used also for electrochemical sensors operating according to the potentiometric principle, in which the oxygen of ambient air is used as a reference material, and the gas to be analyzed is admitted to the sensor or measuring electrode 38. For such applications, the layer 42 providing for access of the gas to be tested to the sensing electrode preferably is much more porous than when the layer 42 is additionally used as a diffusion barrier for a sensor operating in a polarographic mode.

Tunnels with a filler material therebeneath can also be used for gas or air ducts for electrodes which are located at the intermediate or at the connecting or terminal end regions of the sensor. The filler material additionally forms a protective layer to protect the electrodes against chemical and mechanical damage.

The sensor elements as described are particularly rugged and sturdy since the tunnel cover layers 44, 51 are supported throughout their extent by the porous fillers 42, 49.

Various changes and modifications may be made, and features described in connection with any one of the embodiments may be used with any of the others within the scope of the inventive concept.

The dimensions given herein are not critical, and suitable for a sensor to determine the oxygen content in the exhaust gases from an automotive internal combustion engine.

We claim:

1. Electrochemical sensor to determine the oxygen content of test gases, particularly to analyze exhaust gases from a combustion process, especially from an internal combustion engine, having a tubular housing (12);

a plate-like sensing element (11, 511) retained in the housing and having a sensing end portion (11/1; 511/1) adapted to be exposed to the gas to be analyzed, an intermediate holding portion (11/2) and a connecting portion (11/3) adapted to be connected to an electrical circuit (B, E), wherein the sensing end portion of the plate-like sensing element comprises an oxygen ion conductive solid electrolyte plate-like carrier (35) having terminal edges;

two layer-like porous electrodes (39, 48; 539, 548), applied to the plate-like carrier and positioned inwardly of the edges of the solid electrolyte plate-like carrier (35), one of the electrodes forming a sensing electrode and being in communication with the gas to be analyzed, and comprising, in accordance with the invention, a sintered, porous, gas-pervious filler material (42, 49) covering at least one of the electrodes (39, 48; 539, 548) and a portion of the carrier, and extending towards and adjacent to a neighboring edge (40) of the carrier;

and a gas-tight covering (44, 51) placed over said porous filler material and the at least one electrode covered by said filler material (42, 49), the edge of the gas-tight covering (44) being forward of the edge of said at least one electrode beneath the filler material to force the gas to flow at least for some distance along the plane of the carrier and hence over said at least one layer-like porous electrode beneath the porous filler material, said gas-tight covering being mechanically supported by the porous filler material over the layer-like electrode applied to the plate-like carrier, and forming a tunnel cover over said porous filler material, the respective electrode therebeneath and said portion of the carrier, the tunnel being filled by said porous filler material, said tunnel extending essentially parallel to the major surface of said electrolyte plate-like carrier (35);

said gas-tight covering leaving exposed a portion of the sintered, porous, gas-pervious filler material in a region adjacent said edge (40) to expose said filler material to the gas to be applied to the electrode in, and beneath the tunnel, to permit access of said gas to the filler material and to conduct said gas along the surface of said carrier portion and hence to the electrode positioned beneath the tunnel cover, said gas-tight covering protecting the electrode and isolating the porous filler material over the carrier portion and over the electrode, and hence the electrode, from contact with gas surrounding said sensing elmeent except at the zone of exposure adjacent said edge.

2. Sensor according to claim 1, further including an electrically insulating layer (37) applied to the solid electrolyte carrier (35);

and a heating element (41) applied to and carried by said insulating layer.

3. Sensor according to claim 2, wherein the gas-tight covering (44) extends over the heating element (41) to form an insulating layer thereover.

4. Sensor according to claim 1, wherein (FIGS. 2-4) each of the major surfaces (36, 45) of the plate-like sensing element has a respective electrode (39, 48) applied thereto.

5. Sensor according to claim 4, wherein the sensing electrode is covered by the porous filler material;

the porous filler material (42, 542) extends up to said edge (40);

and the gas-tight cover (44, 51; 544) terminates short of said edge and leaves an exposed portion (43, 543) of the sintered, porous, gas-pervious filler material (42, 542) in the region of the sensing end portion to permit passage of oxygen molecules from the gas to be analyzed through said gas-pervious filler material to the sensing electrode, while protecting the sensing electrode against contact with other gases.

6. Sensor according to claim 5, wherein the other of the electrodes (49, 549) forms a reference electrode;

the sintered, porous, gas-pervious filler material (49, 549) extends to the connected portion (11/3) of the plate-like sensing element;

and the gas-tight covering (51, 544) covers the filler material in the region of a first edge exposed to the test gases to inhibit access of test gases to the filler in the region of said first edge, while leaving free a region or zone (50, 550) of said gas-pervious filler material adjacent the connecting portion (11/3) of the plate-like sensing element to permit access of oxygen from ambient air to said gas-pervious filler material and hence to the reference electrode (48, 548).

7. Sensor according to claim 4, wherein one of the electrodes (48, 548) forms a reference electrode;

the sintered, porous, gas-pervious filler material (49, 549) extends to the connecting portion (11/3) of the plate-like sensing element;

and the gas-tight covering (51, 544) covers the filler material in the region of a first edge exposed to the test gases to inhibit access of test gases to the filler in the region of said first edge, while leaving free a region or zone (50, 550) of said gas-pervious filler material adjacent the connecting portion (11/3) of the plate-like sensing element to permit access of oxygen from ambient air to said gas-pervious filler material and hence to the reference electrode (48, 548).

8. Sensor according to claim 1, wherein (FIG. 5) the electrodes (539, 548) are located at the same side of the plate-like sensing element (511/1), spaced from each other.

9. Sensor according to claim 8, wherein the sensing electrode is covered by the porous filler material;

the porous filler material (42, 542) extends up to said edge (40);

and the gas-tight cover (44, 51; 544) terminates short of said edge and leaves an exposed portion (43, 543) of the sintered, porous, gas-pervious filler material (42, 542) in the region of the sensing end portion to permit passage of oxygen molecules from the gas to be analyzed through said gas-pervious filler material to the sensing electrode, while protecting the sensing electrode against contact with other gases.

10. Sensor according to claim 9, wherein the other of the electrodes (49, 549) forms a reference electrode;

the sintered, porous, gas-pervious filler material (49, 549) extends to the connection portion (11/3) of the plate-like sensing element;

and the gas-tight covering (51, 544) covers the filler material in the region of a first edge exposed to the test gases to inhibit access of test gases to the filler in the region of said first edge, while leaving free a region or zone (50, 550) of said gas-pervious filler material adjacent the connecting portion (11/3) of the plate-like sensing element to permit access of oxygen from ambient air to said gas-pervious filler material and hence to the reference electrode (48, 548).

11. Sensor according to claim 8, wherein one of the electrodes (48, 548) forms a reference electrode;

the sintered, porous, gas-pervious filler material (49, 549) extends to the connecting portion (11/3) of the plate-like sensing element;

and the gas-tight covering (51, 544) covers the filler material in the region of a first edge exposed to the test gases to inhibit access of test gases to the filler in the region of said first edge, while leaving free a region or zone (50, 550) of said gas-pervious filler material adjacent the connecting portion (11/3) of the plate-like sensing element to permit access of oxygen from ambient air to said gas-pervious filler material and hence to the reference electrode (48, 548).

12. Sensor according to claim 1, further including conductive tracks (39', 48'; 539', 548') connected to respective electrodes and extending from the electrodes to the connecting portion, said conductive tracks terminating in metallic free end regions to permit electrical connection to an external circuit (B, E).

* * * * *